United States Patent [19]

Pritty

[11] 4,239,958
[45] Dec. 16, 1980

[54] APPARATUS FOR USE IN ORDERING TRIALS

[75] Inventor: David W. Pritty, Glasgow, Scotland

[73] Assignee: University of Strathclyde, Glasgow, Scotland

[21] Appl. No.: 20,248

[22] Filed: Mar. 13, 1979

Related U.S. Application Data

[63] Continuation-in-part of Ser. No. 830,015, Aug. 30, 1977, abandoned.

[51] Int. Cl.³ .............................................. G06M 3/14
[52] U.S. Cl. ......................... 235/92 AC; 235/92 MS; 434/238
[58] Field of Search ......... 235/92 AC, 92 FP, 92 SB, 235/92 CV, 92 CA; 324/62 R, 57 R; 35/22 A, 22 R, 19 A

[56] References Cited

U.S. PATENT DOCUMENTS

| | | | |
|---|---|---|---|
| 3,436,530 | 4/1969 | Faude et al. .................... 235/92 AC |
| 3,490,039 | 1/1970 | Tsao ................................... 324/62 R |
| 3,551,652 | 12/1970 | Faude ............................. 235/92 FP |
| 3,786,350 | 1/1974 | Munt .................................. 324/62 R |

Primary Examiner—Joseph M. Thesz
Attorney, Agent, or Firm—Mason, Fenwick & Lawrence

[57] ABSTRACT

Apparatus for conducting Ordering Trials including a set of counters each incorporating an electrical circuit element which covertly identifies that counter and a box having locations for receipt of the counters. The counters and locations are fitted with plugs and sockets which are interengageable and permit the circuit element to be connected to electrical read-out circuitry which includes circuitry for identifying which counter is in which location. An arithmetic unit operating according to a predetermined algorithm is connected to the output of the interrogation circuitry to provide a measure of the result of a trial. The invention is concerned with a form of interrogation circuitry which permits a direct digital readout to be attained.

4 Claims, 9 Drawing Figures

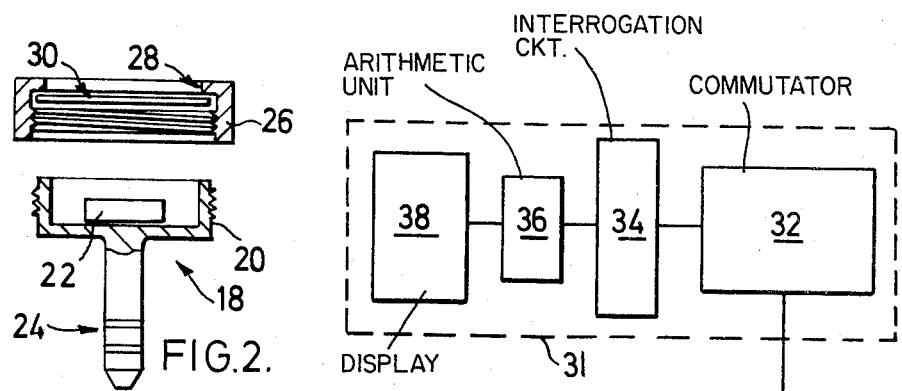
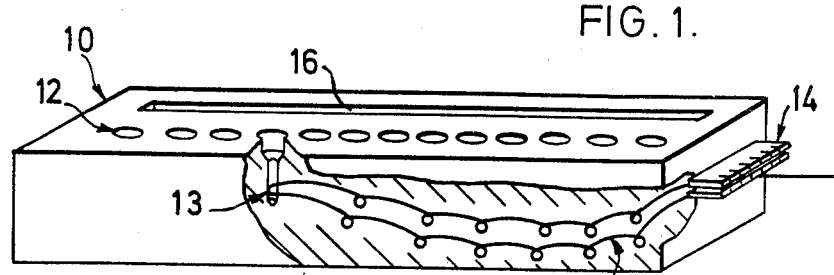
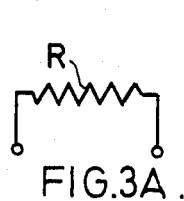
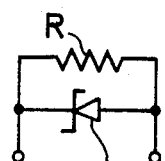
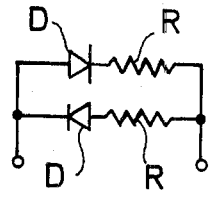
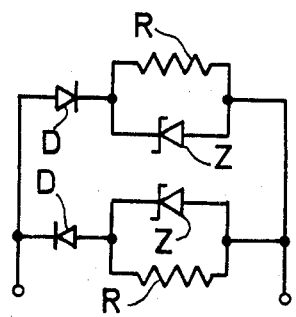
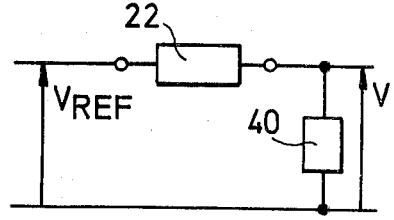
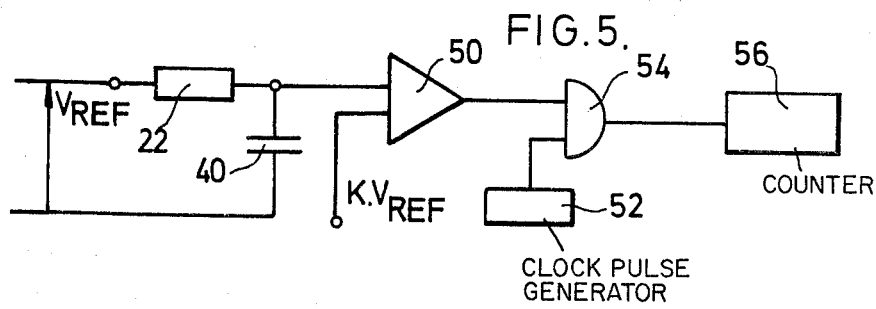

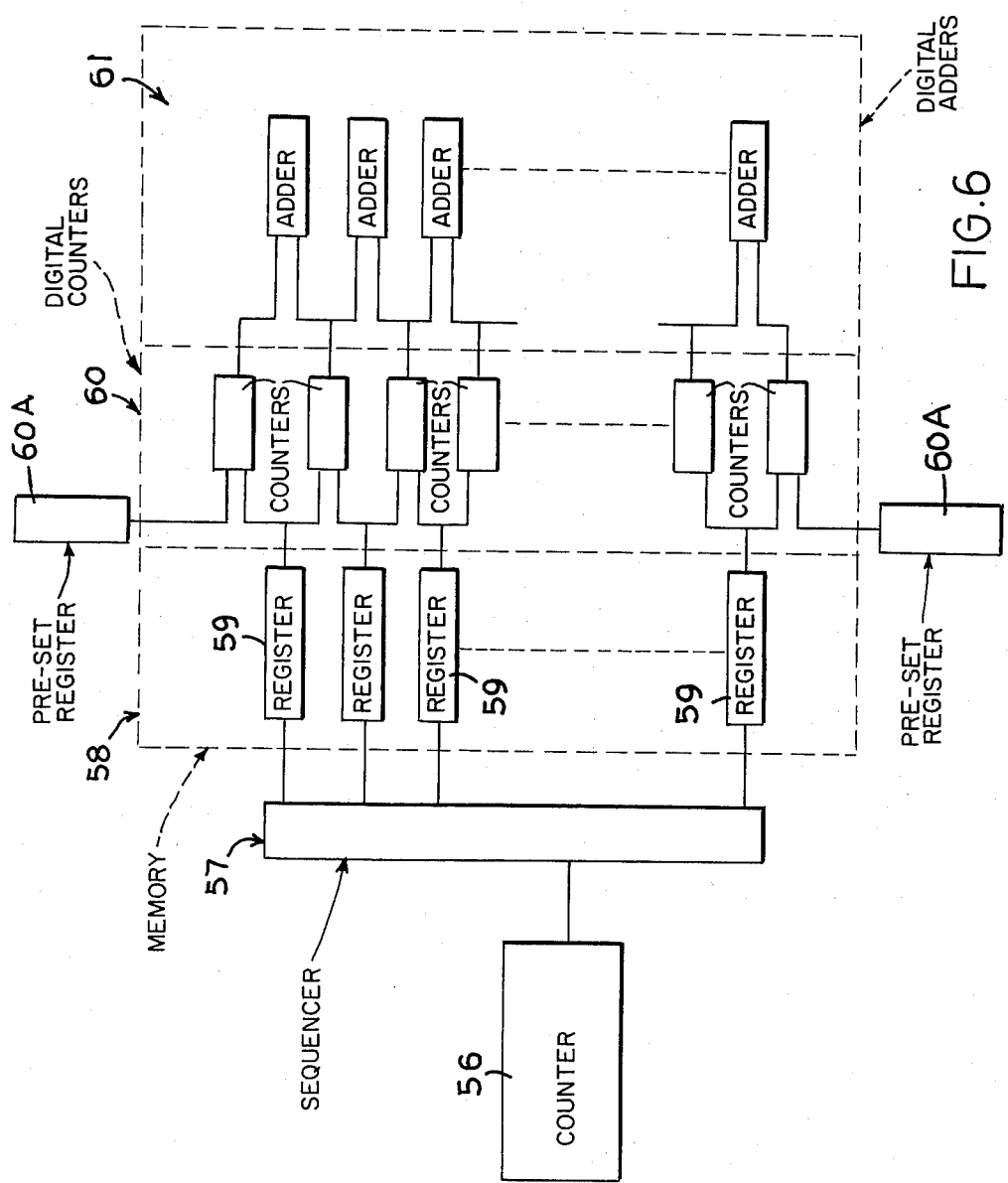

APPARATUS FOR USE IN ORDERING TRIALS

This application is a continuation-in-part of my earlier application Ser. No. 830,015 filed Aug. 30, 1977, now abandoned.

This invention relates to apparatus for use in conducting and in assessing the results from Ordering Trials undertaken by a subject.

Ordering Trials are well known and they usually require the subject to arrange in sequence a set of objects respectively having unique characteristics. Thus, for example, where the unique characteristic is colour tone or hue the requirement of the Trial is to arrange different colour tones or hues in order. The 100- hue test introduced by Farnsworth and described in J.O.S.A. volume 33 page 568 (published 1943) operates on this basis and has found a wide and continuing use in both clinical and research practice in relation to colour vision deficiencies.

In order to measure the result of a Trial scoring systems have been evolved which rely upon the aggregation of errors caused by incorrectly ordering each object in relation to its neighbouring objects or in relation to its true location. Hitherto scoring according to these scoring systems has had to be undertaken manually utilising numbers printed on each object at a location hidden from the view of the subject. This has meant that measuring the result of the trial has been tedious and very time consuming to such an extent that it has effectively precluded a subject from repeatedly undertaking the same Trial, whereby statistically more accurate information might be derived from the set of Trials.

Co-pending application, Ser. No. 811,838 filed June 28, 1977 by Gordon B. Donaldson and assigned to the University of Strathclyde, now abandoned, discloses an improved form of apparatus for use in conducting ordinary trials which permits simplification in measuring the trial result. The improved form of apparatus of the Donaldson application includes a set of counters respectively having unique characteristics, the sequential ordering of which is to be undertaken by a subject, with each counter including at least one electrical circuit element. The electrical characteristic of the circuit element or elements uniquely identifies that counter, and a holder is provided having a set of identical locations respectively for receiving one of the counters. The holder includes a plurality of electrical conductors associated respectively with those locations, and interengageable electrical terminals are provided at the locations and on the counters so that when a particular location receives a particular counter the electrical circuit element of that counter is connected electrically to the pertaining electrical conductors. Readout means are connected to the electrical conductors and incorporate interrogation circuitry which is operable to determine the electrical characteristics of the counters in the respective locations and an arithmetic unit operating according to a predetermined algorithm is connected to the output of the interrogation circuitry to provide a measure of the result of a trial.

The present invention has for its object further to simplify the Donaldson apparatus whereby a digital readout can be obtained in a simple manner. The present invention therefore provides that the interrogation circuitry comprises a reference impedance in the form of a capacitor connectible in series with said circuit element and with a source of reference voltage, the voltage across the capacitor being fed as one input of a comparator having as its other input a voltage of value very much less than said reference voltage, the output of the comparator being connected to a two-input AND gate having its output connected to a counter, and its other input connected to a clock pulse generator.

An embodiment of the present invention will now be described by way of example with reference to the accompanying drawings, in which:

FIGS. 1-4 illustrate the Donaldson apparatus, FIGS. 1 and 2 being partly block and partly schematic in form, FIGS. 3A to 3D showing alternative electrical circuit configurations of a detail of the apparatus, and FIG. 4 being a circuit diagram of another detail;

FIG. 5 is a block diagram illustrating the present invention, and

FIG. 6 is a block diagram showing an implementation of an algorithm for evaluating a Trial.

In order to conduct a colour-vision Ordering Trial a box 10 is provided having a plurality of sockets 12 arranged in a row, these sockets 12 incorporating electrical connectors 13 which are coupled by way of electrical conductors 15 to a terminal block 14 at one end of the box 10. Within the box 10 and temporarily stored in a storage recess 16 is a set of counters 18 which are individually movable from the recess 16 to any one of the sockets 12. For this purpose each counter 18 is as shown in FIG. 2 i.e. comprising a cup-shaped member 20 within which is located an electrical circuit element 22 electrically-connected to a Jack plug 24 mounted on the base of the member 20. The Jack plug 24 is dimensioned to fit each of the sockets 12. The member 20 is externally screw-threaded and receives a screw-threaded cap 26 which is apertured at 28 and acts as a frame and clamp to secure a coloured disc 30 to the member 20. Each cap 26 is made of black plastics and the discs 30 vary in colour from counter to counter. Thus the counters 18 respectively have unique visual characteristics and by virtue of the arrangement of Jack plug and socket 24, 16 the counters 18 can be interchangeably located in the sockets 12 where the electrical connectors 13 and the terminal block 14 permit the nature of the electrical characteristic of each counter (which varies from counter to counter) to be interrogated by a read-out 31.

The read-out 31 includes a commutator 32 whereby each of the electrical connectors 13 is connected in sequence to interrogation circuitry 34 which is operable to determine the electrical characteristic of the elements 22 forming part of the respective counters 18. At the output of the circuitry 34 there is an arithmetic unit 36 which operates either in analogue or digital mode according to a predetermined algorithm (as will be explained) to provide a measure of the result of a trial which is displayed in a display unit 38.

The form of the read-out 31 is in part dictated by the form of the circuit element 22 of the counter 18 and in part by the number of counters 18 which determine the degree of discrimination required. Thus, for example the element 22 may take the form of a resistor (R) having a different value in each counter 18. Alternatively, the element 22 may take the form of a parallel combination of resistor (R) and zener diode (Z) the values of each of which differ from counter to counter. Alternatively the element 22 may incorporate resistors (R) and diodes (D) or resistors (R), zeners (Z) and diodes (D), with the diodes connected in parallel circuits with reversed polarity. These alternatives are illustrated in FIGS. 3A–D and in each case the interrogator 34 of the read out 31 is arranged as shown in FIG. 4 to connect the element 22 in series with a reference element 40, to apply a reference voltage ($V_{REF}$) to the series combination, and to feed the voltage (V) appearing across the reference element 40 to the arithmetic unit 36 as a measure of the magnitude of the element 22.

To illustrate the operation of the circuit shown in FIG. 4 in the simplest case where the element 22 is a single resistor and the reference element 40 is also a single resistor, it follows that $$V = \frac{R_{40} \cdot V_{REF}}{R_{40} + R_{22}}$$

from which the arithmetic unit 36 can operate on the basis that $$R_{22} = \frac{R_{40}(V_{REF} - V)}{V}$$

whereby to evaluate $R_{22}$ and, in turn, to identify the counter concerned.

The arithmetic unit 36 can operate on an analogue basis utilising the voltage V of FIG. 4. Alternatively the voltage V may be digitised by comparison with a staircase waveform and the arithmetic unit 36 may then operate on a digital basis.

The arithmetic unit 36 in addition to evaluating $R_{22}$ also scores the Ordering Trial in accordance with a predetermined algorithm. For example one algorithm commonly used in the Farnsworth Test is to determine an "error value" for each socket 12 by initially evaluating $R_{22}$ for the counter in each socket, computing the numerical difference (scalar) between the thus identified counter values of adjacent sockets, and for each socket, adding adjacent differences. These error values are then displayed in graphical form in the display 38 and are aggregated and displayed as an aggregate error figure for the trial. The graphic part of the display 38 is conventionally plotted in polar co-ordinates, radial dimension indicating error values and the angular dimension representing the different sockets 12.

In the case where the element 22 is of the form illustrated in FIG. 3B the value of the element 22 is represented in a two-digit system of which the resistor provides one digit and the zener provides the other digit. The interrogator unit 34 operates in two stages: applying a first reference voltage large enough to turn on the zener of all the counters whereby to give an output that is independent of resistance value but dependent upon individual zener voltage drop; and a second reference voltage low enough to prevent any zeners from conducting whereby to give an output which is independent of zener voltage drop but is dependent on resistance value.

In the case where the element 22 is of the form illustrated in FIG. 3C the value of the element is ascertained as previously described with reference to FIG. 3A but utilising a first reference voltage of say positive polarity and then a second reference voltage of the opposite polarity. Likewise, when the elements 22 are in the form of FIG. 3D the procedure described above in relation to FIG. 3B can be utilised with reference voltages of say positive polarity followed by negative polarity reference voltages to evaluate the element.

In accordance with the present invention where the element 22 of the counters 18 is of the form shown in FIG. 3A the interrogator unit 34, while maintaining the circuit of FIG. 4 may utilise a capacitor as the element 40 and may directly convert the voltage V into digital format. This can be achieved by utilising the circuit of FIG. 5. With this circuit when the reference voltage is applied the voltage V rises and approaches the limiting value $V_{REF}$ in an exponential fashion. This voltage V is applied as one input of a comparator 50 the other input of which is a voltage $K \cdot V_{REF}$ where K is a constant of value very much less than unity. The output of the comparator and the output from a 1 MHz clock pulse generator 52 are both applied as inputs to an AND gate 54 and the output of the gate 54 is applied to a counter 56. A logic unit (not shown) is arranged to control the circuit such that when $V_{REF}$ is applied the comparator output enables the gate 54 and permits the clock pulses to accumulate in the counter 56. When the voltage V reaches the $K \cdot V_{REF}$ level the comparator output reverses and disables the gate 54. Thus, the count in the counter 56 is a measure of the time taken for capacitor 40 to charge to the $K \cdot V_{REF}$ level and this in turn is directly dependent upon the value of the resistor 22.

The circuit of FIG. 5 is simple to control to determine the resistance values of elements 22 forming a set if the resistance values are about 20% apart, e.g., 1.5 K, 1.8 K, 2.2 K, 2.7 K ohms and of course, between evaluations it is necessary to discharge the capacitor 40 and to reset the counter 56 to zero. By way of example, and to implement the previously described algorithm, the arithmetic unit 36 may contain the circuitry of FIG. 6 where the output of counter 56 is fed to a sequencer 57 so that the respective values of the resistors 22 are fed to a memory 58 containing a plurality of digital registers 59, one for each of the counters 18 and in this way the values of the counters 18 are stored in the memory 58. The individual registers 59 feed into digital counters 60 arranged respectively to subtract the values fed thereto from adjacent registers 59 so that the counters 60 output the "difference values" referred to previously and adjacent counters 60 feed into digital adders 61 so as to add adjacent difference values thereby to evaluate an error value for each counter 18 as previously described. The outputs from the adders 61 are fed to the display unit 38 for display in the desired manner. Because there is one more counter 60 than registers 59 the first and last counter 60 each has one input supplied by preset registers 60A.

In a satisfactory embodiment, the counters 56 may produce numbers linearly related to the resistors forming the circuit elements 22 and the memory 58 receives numbers linearly related to the numbers on the caps 26. For example, the numbers produced by the counter 56 or applied to the memory 58 may be digital numbers such as 8 bit numbers. In one satisfactory example, the components forming the blocks indicated in FIG. 6 may each be of the Texas Instruments 74 series TTL logic range. Thus block 57 may be made up of inverters, buffers, counters, decoders and a sequencer clock controlled by standard 74 series TTL logic, all formed of Texas Instruments 74 series off-the-shelf Integrated Circuit components, as will be well recognized by those skilled in the art.

Similarly, the registers 59 and 60A may be Texas Instruments 74 series bit registers, the counters 60 may be formed of 74 series inverters, adders and a register, and the adders 61 may be 74 series adders and registers, all of which are also Texas Instruments 74 series off-the-shelf Integrated Circuits.

Because the arithmetic unit 36 operates in digital format its logic circuitry controlling the algorithm of operation can readily be altered in any desired manner. Furthermore the error values and the enumerated values of the counters can be stored in a digital memory system for subsequent use by the display unit 38. This arrangement has the advantage that the scale factor for the polar chart can be determined after completion of all the error values by the arithmetic unit 36 in order that the most advantageous presentation of the information can be affected. Furthermore, although it is preferred to plot socket location in sequence angularly on the chart the display could be arranged to associate error values with counter numbers which would then be displayed angularly in sequence.

The commutator 32 may take any convenient form such as a diode network operated by control logic or it may take the form of a plurality of transistor switches operated sequentially by control logic. Alternatively the commutator 32 may incorporate minaturised reed switches.

The number and shape of the boxes 10 is not important to the present invention. Conveniently however the boxes are four in number each being connected to the read out 31, whereby the coloured discs 30 may be arranged in sub-groups one to each box. In an alternative form the sockets 12 are arranged in a closed loop. Although the components 20, 26 of the counters 18 are illustrated as being connected by a screw thread they could, of course, be manufactured to permit connection by a simple push fit.

What is claimed is:

1. In apparatus for use in conducting Ordering Trials, a set of counters respectively having unique characteristics the sequential ordering of which is to be undertaken by a subject,
a holder having a set of identical locations respectively for receiving a said counter,
each counter comprising at least one electrical circuit element the electrical characteristic of which uniquely identifies that counter, the holder comprising a plurality of electrical conductors associated respectively with said locations, interengageable electrical terminals provided at said locations and on the counters such that when a particular location receives a particular counter the electrical circuit element of that counter is connected electrically to the pertaining electrical conductors, read-out means connected to said electrical conductors, said read-out means incorporating interrogation circuitry which is operable to determine the electrical characteristics of the counters in the respective locations, and an arithmetic unit operating according to a predetermined algorithm and connected to the output of the interrogation circuitry to provide a measure of the result of a trial,
each counter having a resistive electrical circuit element, and said interrogation circuitry comprises a reference impedance in the form of a capacitor connectible in series with said circuit element and with a source of reference voltage, the voltage across the capacitor being fed as one input of a comparator having as its other input a voltage of value very much less than said reference voltage, the output of the comparator being connected to a two-input AND gate having its output connected to a counter, and its other input connected to a clock pulse generator.

2. Apparatus as claimed in claim 1, wherein said interengageable electrical terminals are in the form of jack plugs and sockets, the jack plugs being mounted on the counters and the sockets forming said locations in the holder.

3. Apparatus as claimed in claim 1, wherein each counter comprises only one electrical circuit element which is in the form of resistance, the resistance value being different for each counter in the set.

4. Apparatus as claimed in claim 1, wherein said interrogation circuitry comprises a reference resistance element connectible in series with said electrical circuit element and with the source of reference voltage.

* * * * *